(12) United States Patent
Cheng et al.

(10) Patent No.: US 9,671,409 B2
(45) Date of Patent: Jun. 6, 2017

(54) ULTRATHIN CALCINATED FILMS ON A GOLD SURFACE FOR HIGHLY EFFECTIVE LASER DESORPTION/IONIZATION OF BIOMOLECULES

(71) Applicant: The Regents of the University of California, Oakland, CA (US)

(72) Inventors: Quan Cheng, Irvine, CA (US); Jicheng Duan, Irvine, CA (US); Matthew James Linman, Riverside, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 14/934,755

(22) Filed: Nov. 6, 2015

(65) Prior Publication Data
US 2016/0202266 A1    Jul. 14, 2016

Related U.S. Application Data

(63) Continuation of application No. 13/698,764, filed as application No. PCT/US2011/000874 on May 18, 2011, now abandoned.
(Continued)

(51) Int. Cl.
*G01N 33/68* (2006.01)
*H01J 49/02* (2006.01)
(Continued)

(52) U.S. Cl.
CPC ......... *G01N 33/6851* (2013.01); *B05D 3/007* (2013.01); *C23C 18/1212* (2013.01);
(Continued)

(58) Field of Classification Search
None
See application file for complete search history.

(56) References Cited

PUBLICATIONS

Karas et al., "Matrix-assisted laser desorption ionization mass spectrometry", Mass Spectrometry Reviews, 1991, 10, pp. 335-357.
(Continued)

*Primary Examiner* — Kaijiang Zhang
(74) *Attorney, Agent, or Firm* — Buchanan Ingersoll & Rooney PC

(57) ABSTRACT

A nanoscale calcinated silicate film fabricated on a gold substrate for highly effective, matrix-free laser desorption ionization mass spectrometry (LDI-MS) analysis of biomolecules. The calcinated film is prepared by a layer-by-layer (LbL) deposition/calcination process wherein the thickness of the silicate layer and its surface properties are precisely controlled. The film exhibits outstanding efficiency in LDI-MS with extremely low background noise in the low-mass region, allowing for effective analysis of low mass weight samples and detection of large biomolecules including amino acids, peptides and proteins. Additional advantages for the calcinated film include ease of preparation and modification, high reproducibility, low cost and excellent reusability. Experimental parameters that influence LDI on calcinated films have been systemically investigated. Presence of citric acid in the sample significantly enhances LDI performance by facilitating protonation of the analyte and reducing fragmentation. The wetting property and surface roughness appear to be important factors that manipulate LDI performance of the analytes. This new substrate presents a marked advance in the development of matrix-free mass spectrometric methods and is uniquely suited for analysis of biomolecules over a broad mass range with high sensitivity.

14 Claims, 11 Drawing Sheets

Related U.S. Application Data

(60) Provisional application No. 61/345,903, filed on May 18, 2010.

(51) Int. Cl.
```
C23C 18/12      (2006.01)
B05D 3/00       (2006.01)
C23C 18/14      (2006.01)
C23C 18/16      (2006.01)
```

(52) U.S. Cl.
CPC ...... *C23C 18/1241* (2013.01); *C23C 18/1283* (2013.01); *C23C 18/14* (2013.01); *C23C 18/165* (2013.01); *H01J 49/02* (2013.01); *Y10T 428/265* (2015.01)

(56) References Cited

PUBLICATIONS

Wei et al., "Desorption-ionization mass spectrometry on porous silicon", Letters to Nature, May 20, 1999, vol. 399, pp. 243-246.
Lo et al., "Surface-Assisted Laser Desorption/Ionization Mass Spectrometry on Titania Nanotube Arrays", American Society for Mass Spectrometry, Apr. 26, 2008, 19, pp. 1014-1020.
Wada et al., "Ordered Porous Alumina Geometries and Surface Metals for Surface-Assisted Laser Desorption/Ionization of Biomolecules: Possible Mechanistic Implications of Metal Surface Melting", Analytic Chemistry, Dec. 1, 2007, vol. 79, No. 23, pp. 9122-9127.
Hoang et al., "Analysis of Organoselenium Compounds in Human Urine Using Active Carbon and Chemically Modified Silica Sol-Gel Surface-Assisted Laser Desorption/Ionization High-Resolution Time-of-Flight Mass Spectrometry", Analytical Chemistry, Apr. 1, 2004, vol. 76, No. 7, pp. 2062-2070.
Dattelbaum et al., Surface assisted laser desorption-ionization mass spectrometry on patterned nanoporous silica thin films, Microporous and Mesoporous Materials, 2008, 114, pp. 193-200.
Chen et al., "Desorption/ionization mass spectrometry on nanocrystalline titania sol-gel-deposited films", Rapid Communications in Mass Spectrometry, 2004, 18, pp. 1956-1964.
Kawasaki et al., "Layer-by-Layer Self-Assembled Multilayer Films of Gold Nanoparticles for Surface-Assisted Laser Desorption/Ionization Mass Spectrometry", Analytical Chemistry, Oct. 1, 2008, vol. 80, No. 19, pp. 7524-7533.
Su et al., "Gold Nanoparticles as Assisted Matrix for Determining Neutral Small Carbohydrates through Laser Desorption/Ionization Time-of-Flight Mass Spectrometry", Analytical Chemistry, Feb. 15, 2007, vol. 79, No. 4, pp. 1626-1633.
McLean et al., "Size-Selected (2-10 nm) Gold Nanoparticles for Matrix Assisted Laser Desorption Ionization of Peptides", Journal of American Chemical Society, 2005, 127, pp. 5304-5305.
Castellana et al., "Tailoring Nanoparticle Surface Chemistry to Enhance Laser Desorption Ionization of Peptides and Proteins", Nano Letters, 2007, vol. 7, No. 10, pp. 3023-3025.
Duan et al., "CHCA-Modified Au Nanoparticles for Laser Description Ionization Mass Spectrometric Analysis of Peptides", American Society for Mass Spectrometry, Apr. 18, 2009, 20, pp. 1530-1539.
Cohen et al., "Small molecule analysis by MALDI mass spectrometry", Anal Bioanal Chem, 2002, 373, pp. 571-586.
Peterson, "Matrix-Free Methods for Laser Desorption/Ionization Mass Spectrometry", Mass Spectrometry Reviews, 2007, 26, pp. 19-34.
Guo et al., "Nanomaterials in mass spectrometry ionization and prospects for biological application", Anal Bional Chem, 2006, 384, pp. 584-592.
Merchant et al., "Recent advancements in surface-enhanced laser desorption/ionization—time of flight—mass spectrometry", Electrophoresis, 2000, 21, pp. 1164-1167.
Wen et al., "Small-Molecule Analysis with Silicon-Nanoparticle-Assisted Laser Desorption/Ionization Mass Spectrometry", Analytical Chemistry, Jan. 15, 2007, vol. 79, No. 2, pp. 434-444.
Tanaka et al., "Protein and Polymer Analyses up to m/z 100 000 by Laser Ionization Time-of-flight Mass Spectrometry", Rapid Communications in Mass Spectrometry, 1988, vol. 2, No. 8, pp. 151-153.
Bi et al., "TiO2 Printed Aluminum Foil: Single-Use Film for a Laser Desorption/Ionization Target Plate", Analytical Chemistry, Feb. 1, 2009, vol. 81, No. 3, pp. 1177-1183.
Go et al., "Desorption/Ionization on Silicon Nanowires", Analytical Chemistry, Mar. 15, 2005, vol. 77, No. 6, pp. 1641-1646.
Zhang, "Label-free Detection of Oligonucleotide Microarrays by the Scanning Kelvin Nanoprobe," Ph.D. dissertation, University of Toronto, 2008.
Grote et al., "Surface Plasmon Resonance/Mass Spectrometry Interface," Anal. Chem. 2005, 77:1157-1162.
Linman et al., "Fabrication of Fracture-Free Nanoglassified Substrates by Layer-by-Layer Deposition with a Paint Gun Technique for Real-Time Monitoring of Protein-Lipid Interactions," Langmuir 2009, 25:3075-3082.

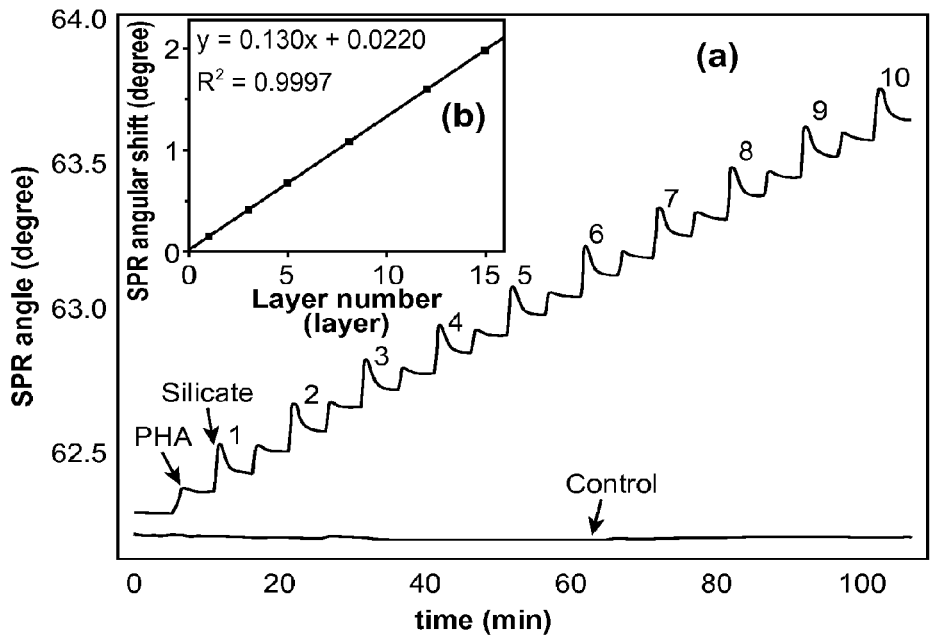
FIG. 8
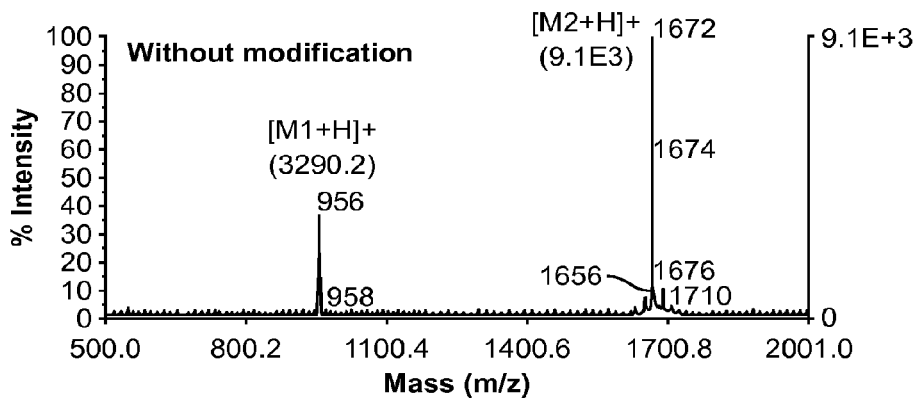
FIG. 9
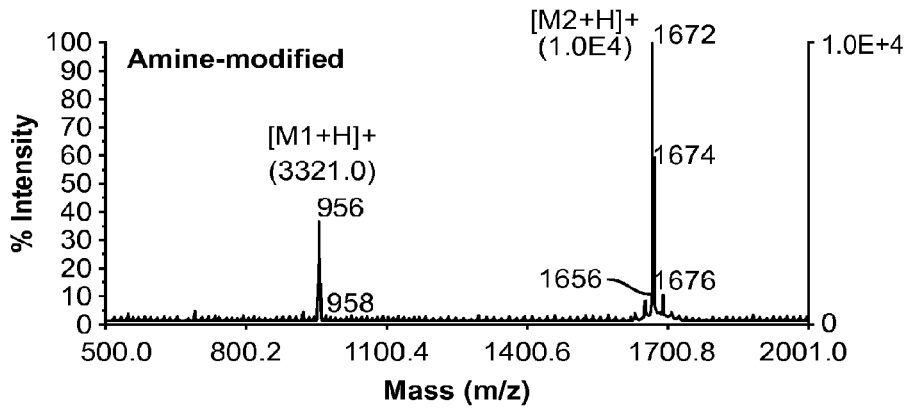

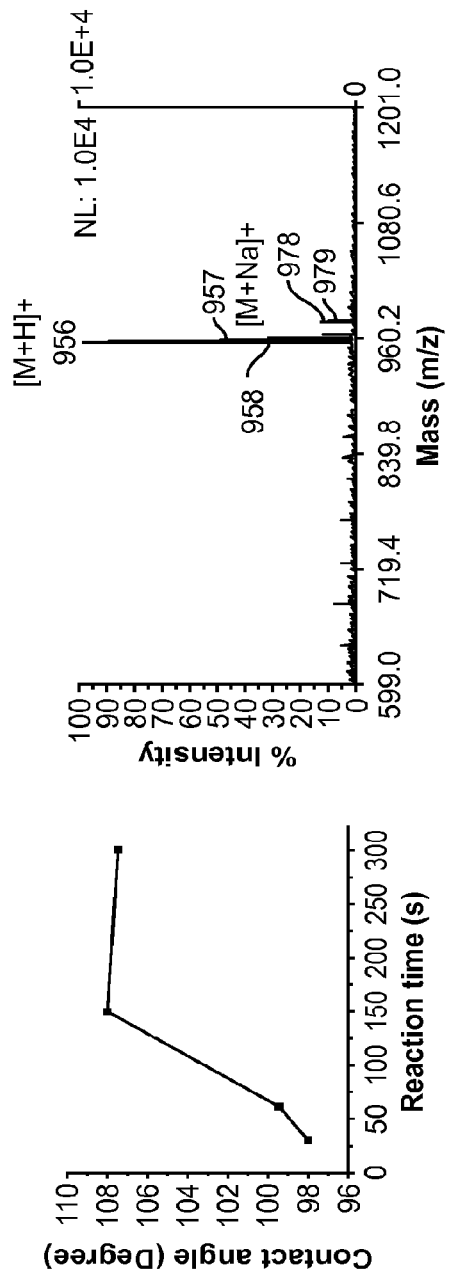
FIG. 10
FIG. 9
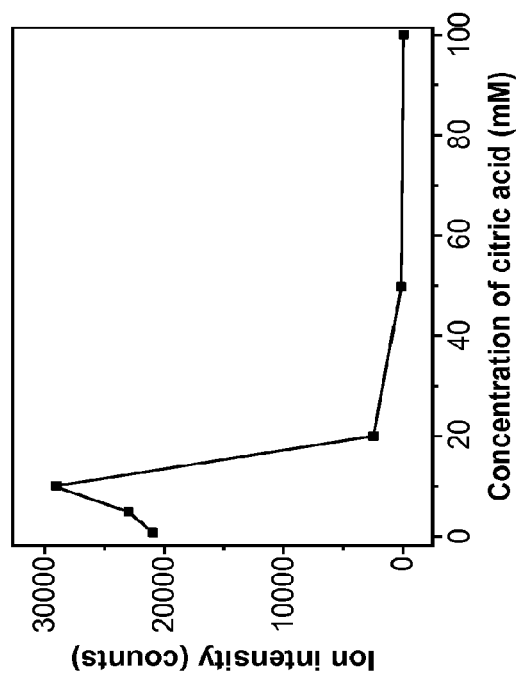
FIG. 11

ULTRATHIN CALCINATED FILMS ON A GOLD SURFACE FOR HIGHLY EFFECTIVE LASER DESORPTION/IONIZATION OF BIOMOLECULES

CROSS-REFERENCE TO RELATED APPLICATION

This patent application claims priority to U.S. Provisional Patent Application Ser. No. 61/345,903, filed May 18, 2010, which is incorporated herein by reference in its entirety.

GOVERNMENT INTEREST

This invention was made with Government support under Grant No. CHE-0719224 awarded by the National Science Foundation (NSF). The Government has certain rights to this invention.

FIELD OF THE INVENTION

This invention relates to a method and system for enhanced laser desorption ionization mass spectrometric (LDI-MS) analysis of biomolecules, and more particularly to an ultrathin calcinated silicate film fabricated on a gold substrate by using a Layer-by-Layer (LbL) deposition/calcination process.

BACKGROUND OF THE INVENTION

The development of soft ionization techniques such as matrix assisted laser desorption ionization (MALDI) has greatly changed the field of mass spectrometric analysis. MALDI-MS benefits from its salt tolerance, simplicity of mass spectra, and broad mass range. Because of the interference from matrix-related ions in low mass range, MALDI-MS is seldom applied to the analysis of low-molecular weight compounds (below 600 Da). This limitation has hampered its wide application in important research fields such as drug discovery and biotechnology, where small molecule detection and identification is of utmost significance. In recent years, various methods leading to direct desorption/ionization without organic matrices have been extensively explored, and surface-assisted laser desorption/ionization (SALDI) has gained considerable attention and has found a broad range of applications in environmental, genomics and proteomics fields owing to its attractive features of simple sample preparation and low background ions. SALDI relies on direct absorption of UV laser light by the substrate or its coating that lead to molecular desorption and subsequent ionization. A range of materials have been investigated for their effective use in SALDI. Nanomaterials in different forms including inorganic powder, nanowire, nanotubes and porous thin structures have been tested as alternatives to organic matrices. Metallic nanoparticles are another family of materials that have been heavily explored. These materials show promising results but also exhibit limitations and have suffered from problems such as inhomogeneous deposition, molecular degradation and interference from metal cluster ions. Among all substrates studied so far, porous silicon (also referred to as desorption/ionization on silicon, DIOS) is the most significant and well-utilized as it offers highly effective ionization due to strong UV adsorption and heat transfer. DIOS substrates are typically prepared by an electrochemical etching procedure. Yet DIOS-MS has limited upper mass range, and the surface is susceptible to oxidation deactivation and requires stringent control of surface physical properties, which must be realized through careful selection of the silicon type and etching conditions, whereas nonuniform surface structures can substantially deteriorate the performance.

A new class of materials based on laser induced electron-phonon interactions for effective desorption/ionization and thus matrix-free mass spectrometric analysis of a range of biomolecules is described herein. In accordance with an exemplary embodiment, a nanoscale, glass-like silicate film fabricated on a thin gold substrate through a layer-by-layer (LbL) deposition/calcination process (FIG. 1) is utilized. There have been reports in literature that use silica ($SiO_2$) and silicate-based materials for SALDI-MS analysis of small molecules. These methods utilize either a sprayed coating of a sol gel solution or a homogenized particle suspension to load the silica to the sample stage for enrichment of samples in SALDI analysis. As a result, the thickness of these layers is in the range of 500-1000 μm and the uniformity is difficult to control. The LbL/calcination process as developed at UC Riverside and described herein, on the other hand, generates a vastly different substrate and allows for precise control of the coating thickness and porosity in the nanometer scale, which is crucial to this ionization method.

In accordance with an exemplary embodiment, the effectiveness of calcinated films on gold for SALDI-MS detection of amino acids, peptides and proteins has been systematically investigated and the substrates are characterized by a number of techniques including scanning electron microscopy (SEM), atomic force microscopy (AFM) and contact angle measurement to understand the relationship between surface property and performance. The ultrathin glassified coating is stable and has high durability, and has a number of other advantages including low cost, well-defined surface property, reusability and ease of preparation and functionalization. In addition, the photonic properties of the thin gold substrate can allow for multiple modes of detection at the same surface and development of new hyphenated technologies.

SUMMARY

In accordance with an exemplary embodiment, a nanoscale film, comprises: a sublayer; and a nanoscale metallic layer with low heat conductivity on the sublayer. In accordance with an exemplary embodiment, the nanoscale metallic layer is preferably a calcinated silicate film.

In accordance with another exemplary embodiment, a nanoscale calcinated silicate film, comprises: a metal sublayer; and a plurality of alternating layers of poly(allylamine hydrochloride) (PAH) and sodium silicate solution on the metal sublayer. In accordance with another exemplary embodiment, the metal sublayer is gold (Au), platinum (Pt), silver (Ag), aluminum (Al) and/or stainless steel.

In accordance with a further exemplary embodiment, a nanoscale calcinated silicate film, comprises: a thin gold layer; and a plurality of alternating layers of poly(allylamine hydrochloride) (PAH) and sodium silicate solution on the thin gold layer.

In accordance with another exemplary embodiment, a calcinated silicate film, comprises: a layer by layer deposition of poly(allylamine hydrochloride) PAH and sodium silicate (water glass) on a gold surface.

In accordance with a further exemplary embodiment, a method of forming a calcinated silicate film comprises: placing a gold layer onto a stainless steel tape and/or glass slide; alternately depositing poly(allylamine hydrochloride) PAH and a sodium silicate solution onto a surface of the gold layer; and calcinating the alternately deposited layers of PAH and sodium silicate solution.

The details of one or more embodiments of the disclosure are set forth in the accompanying drawings and the description below. Other features, objects, and advantages will be apparent from the description and drawings, and from the claims.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention. In the drawings.

FIG. 8 are SPR sensorgrams showing LbL deposition of (PAH/silicate) layers, and wherein insert (b) shows the correlation of the SPR angular shift and the number of (PAH/silicate)$_n$ layers.

FIG. 9 is a comparison between the bare and amine-modified calcinated substrate in SALDI-MS analysis of peptides. Samples: [Sar$^1$, Thr$^8$]-angiotensin II (M1, MW=956.1) and neurotensin (M2, MW=1672), 20 pmol each in 10 mM citric acid (as shown, there is no obvious change in SALDI performance after (3-aminopropyle) triethoxysilane (APTES) modification of the calcinated substrate).

FIG. 10 is a SALDI-MS analysis for [Sar$^1$, Thr$^8$]-angiotensin II (20 pmol) with octadecyltrichlorosilane (OTS)-modified calcinated substrate, and wherein Left: Contact angles increase with the reaction time; and Right: mass spectrum generated with substrate modified with 2% OTS in toluene for 150 seconds.

FIG. 11 is a chart showing the effect of concentration of citric acid on LDI performance with the calcinated surface. Sample: [Sar$^1$, Thr$^8$]-angiotensin II MW=956.1), 20 pmol.

DETAILED DESCRIPTION

Figure 1:
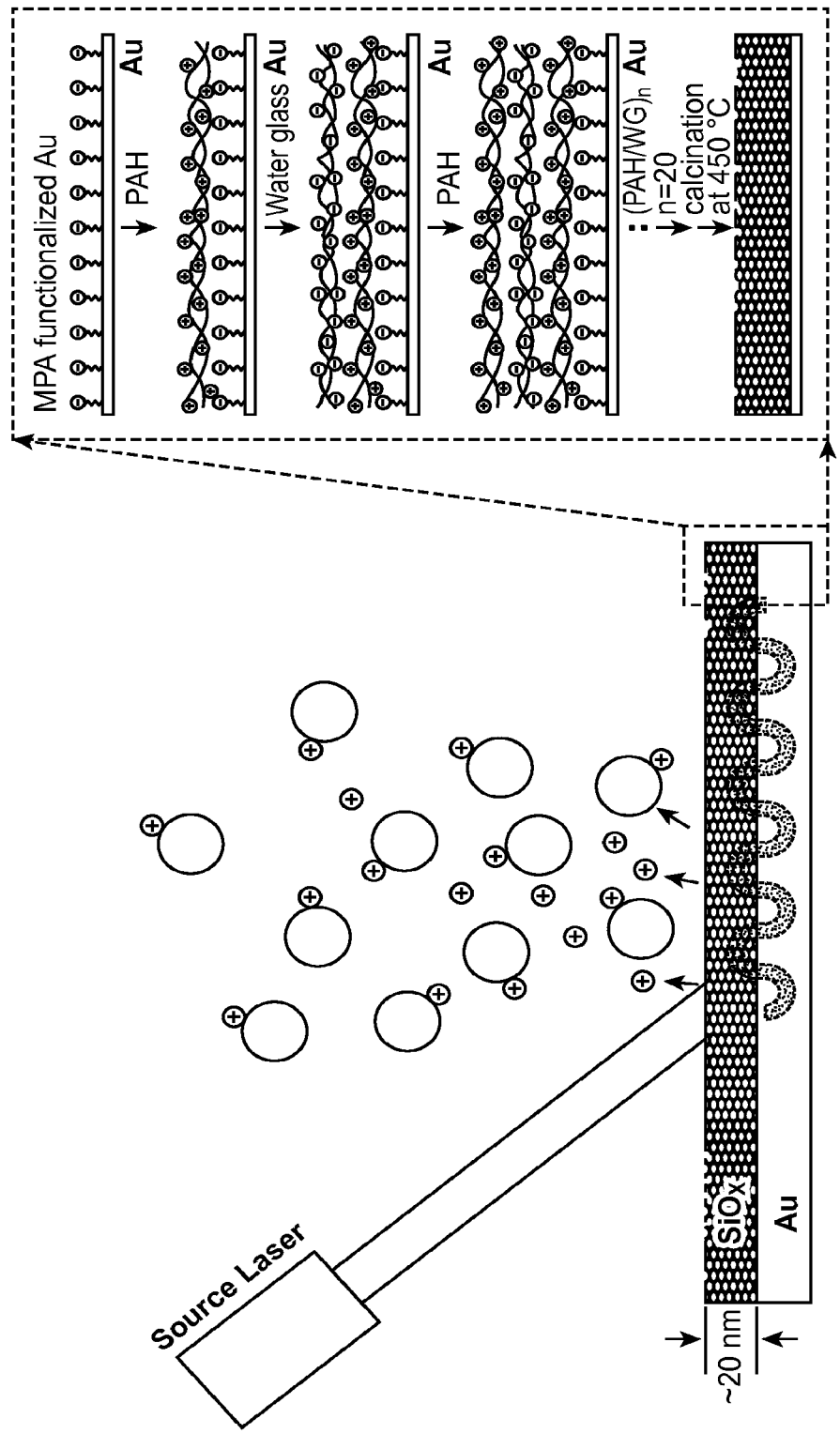
FIG. 1 shows a schematic of SALDI-MS detection with the calcinated silicate film and its fabrication by LbL deposition of PAH and sodium silicate (water glass) on a gold surface.

In accordance with an exemplary embodiment, a nanoscale calcinated silicate film fabricated on a gold substrate for highly effective, matrix-free laser desorption ionization mass spectrometry (LDI-MS) analysis of biomolecules is disclosed herein. In accordance with an exemplary embodiment, the calcinated film is prepared by a layer-by-layer (LbL) deposition/calcination process wherein the thickness of the silicate layer and its surface properties are precisely controlled. The film exhibits outstanding efficiency in LDI-MS with extremely low background noise in the low-mass region, allowing for effective analysis of low mass weight samples and detection of large biomolecules including amino acids, peptides and proteins. Additional advantages for the calcinated film include ease of preparation and modification, high reproducibility, low cost and excellent reusability.

Experimental parameters that influence LDI on calcinated films have been systemically investigated. In addition, the presence of citric acid in the sample significantly enhances LDI performance by facilitating protonation of the analyte and reducing fragmentation. The wetting property and surface roughness appear to be important factors that manipulate LDI performance of the analytes. This new substrate presents a marked advance in the development of matrix-free mass spectrometric methods and is uniquely suited for analysis of biomolecules over a broad mass range with high sensitivity. It can be appreciated that the calcinated film herein may open new avenues for developing novel technology platforms upon integration with existing methods in microfluidics and optics.

Materials and Instrument

3-Mercaptopropionic acid (3-MPA), poly(allylamine hydrochloride) (PAH), α-cyano-3-hydroxy-cinnamic acid (CHCA), [Sar[1], Thr[8]]-angiotensin II (MW=956.1), neurotensin (MW=1672), insulin b chain (oxidized, MW=3495.9) and cytochrome c from bovine heart were purchased from Sigma-Aldrich (St. Louis, Mo.). Sodium silicate ($SiO_x$), citric acid, trifluoroacetic acid (TFA), L(+)-lysine monohydrochloride, L(+)-arginine, L-histidine and acetonitrile were from Thermo-Fisher Scientific (Pittsburgh, Pa.). Stainless steel tape (SST) was purchased from LabelValue.com (Tampa, Fla.). Water was purified by a Milli-Q system. All other reagents were analytical grade and used without further purification.

Preparation of Thin Au Layer (Gold Layer) on Substrates

A gold (Au) surface was fabricated by e-beam deposition of a 46-nm thick gold layer onto pre-cleaned SST and glass slides. 2-nm Cr film was pre-deposited on glass as an adhesion layer before Au deposition to enhance stability of the Au film on the substrate.

It can be appreciated that although the exemplary embodiments as described herein use gold as the sublayer, in accordance with another exemplary embodiment, the sublayer is a metal sublayer, such as stainless steel or stainless steel tape, Pt (platinum), Ag (silver), and/or Al (aluminum). For example, both Ag (silver) and Al (aluminum) can also be used for surface plasmon work, similar to the use of Au (gold) for such work. In addition, the metal sublayer (e.g., Au) can have a thickness of approximately 10 to 2000 nm without departing from the present invention.

Preparation of Nanoscale Calcinated Films

In accordance with an exemplary embodiment, cleaned gold substrates were immersed in a 5 mM 3-MPA ethanol solution overnight, followed by extensive rinsing with ethanol and DI water. PAH (1 mg/mL, pH 8.0) and sodium silicate solution (22 mg/mL, pH 9.5) were alternately deposited to the surface by spray bottles with rinse with DI water between each spray. This process was repeated until the designated number of layers was reached while SPR monitoring was used for quality control. Finally, deposited substrates were calcinated in a furnace by heating to 450° C. at a rate of 17° C. per min and brought to room temperature after 4 hours.

Sample Preparation for MS Analysis

The stock solution for peptides was prepared by dissolving [Sar[1], Thr[8]]-angiotensin II and neurotensin in 50% acetonitrile (ACN) to a concentration of 200 µM, respectively. CHCA solution (10 mg/mL) was prepared in 60% ACN/water solution containing 0.1% TFA. When CHCA was used as the matrix, the sample solution was prepared in a 1:10 ratio of peptide solution to CHCA. For MALDI-MS analysis, 1.0 µL of sample solution was deposited onto the MALDI sample plate and dried in vacuum prior to MS detection.

Calcinated substrates were first washed by DI water and ethanol, and dried by compressed air. The cleaned substrates were attached onto an MALDI plate by adhesive polyimide film tape before samples deposition. Amino acids, peptides and proteins were dissolved in a 60% ACN/water solution containing 0.1% TFA and 10 mM citric acid. Aliquots (0.5-1.0 µL) of sample solution were deposited onto the calcinated surface and allowed to dry in air before SALDI-MS analysis.

Scanning Electron Microscopy (SEM) and Atomic Force Microscopy (AFM)

Scanning electron microscopy (SEM) images were obtained by a Philips XL30 FEG scanning electron microscope system. The SEM measurements were carried out with a beam power of either 5 or 20 kV with magnification ranging from 10× to 80000×. AFM images were collected by a Veeco Dimension 5000 atomic force microscope (Santa Barbara, Calif.) with manufacturer-provided software. All images were obtained in the tapping mode, and RMS surface roughness values were obtained by averaging multiple 5 µm$^2$ areas across the entire substrate at a scan rate of 1.5 Hz.

Contact Angle Measurements

Contact angle measurements were performed on a home built device with deionized water (1 µL). The images for water droplets on substrate were collected by a computer controlled 12-bit cooled CCD camera. All measurements were made in ambient atmosphere at room temperature.

LDI-TOF MS

Laser desorption and matrix assisted laser desorption/ionization mass spectra were obtained by using Voyager-DE STR MALDI-TOF mass spectrometer (Applied Biosystems, USA) operating in positive reflector mode. The mass spectrometer is equipped with a pulsed nitrogen laser operated at 337 nm with 3 ns-duration pulses. The accelerating voltage, grid voltage and extraction delay time were set as 20 kV, 65% and 190 ns, respectively. MS spectra were acquired as an average of 100 laser shots.

Fabrication of Nanoscale Gold/Calcinated (Silicate) Chips

FIG. 1 shows a schematic of SALDI-MS detection with the calcinated chip and its fabrication with LbL deposition of poly(allylamine hydrochloride) (PAH) and sodium silicate (water glass) on an Au-covered stainless steel tape (SST). The layer thickness and other properties of the thin film were monitored with SPR, which was performed on a glass slide based Au substrate under identical deposition conditions. A linear relationship was found between SPR angle shift and deposition layer number, demonstrating a uniform growth of PAH/silicate layers (supplement). The thickness of PAH/silicate layers can be calculated by fitting to theoretical reflectivity curves from the Fresnel equations with an average refractive index (RI) of 1.455 for one PAH/silicate layer. After achieving designated thickness and calcination at 450° C., organic components are removed from the multilayer structure, leading to a reduction of thickness in the film, as indicated in the SPR sensorgram. Using this method, the thickness of the glassified layer can be controlled at 1 nm resolution. From the SPR angular shift, the 15-layer film after calcination has an average thickness of approximately 20 nm.

SALDI-MS on Nanoscale Calcinated Surface

Figure 2:
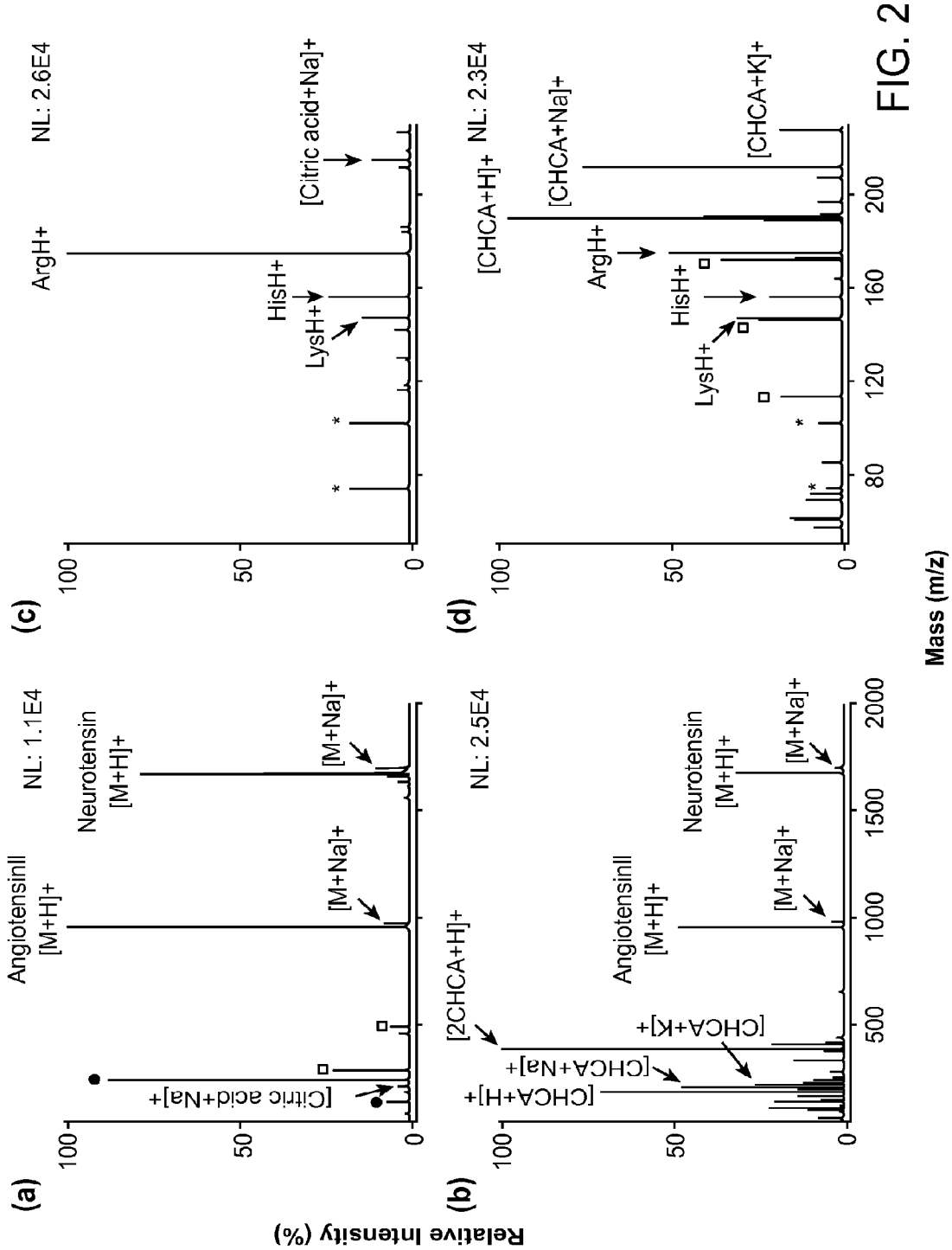
FIG. 2 shows mass spectra for peptides and amino acids as follows: (a) a peptide mixture on calcinated glass surface; (b) a peptide mixture with CHCA matrix; (c) an amino acid mixture on calcinated glass surface; and (d) an amino acid mixture with CHCA matrix. Peptide mixture: [Sar$^1$, Thr$^8$]-angiotensin II MW=956.1) and neurotensin (MW=1672), 20 pmol each with 10 mM citric acid; Amino acid mixture: Lys, His and Arg, 60 pmol each with 10 mM citric acid. ●: impurity ions; □: citrate related ions; *: impurities in amino acid samples; ■: CHCA fragment ions.

The SALDI analysis on nanoscale calcinated surface was carried out with two peptides, [Sar1, Thr8]-angiotensin II (MW 956.1) and neurotensin (MW 1672). FIGS. 2a and 2b show mass spectra of the peptides on the calcinated surface and the MALDI analysis with CHCA matrix for comparison. SALDI on the calcinated surface demonstrated a very clean mass spectrum free of major noise peaks. Peptide protonated ions were dominant in the spectrum with little or no fragmentation, which clearly demonstrated excellent performance of this surface for MS analysis. For MALDI-MS with CHCA, a high background noise appeared in the low-mass region. Matrix related ions, such as [CHCA+H]$^+$ at m/z 190, [CHCA+Na]$^+$ at m/z 212, [CHCA+K]$^+$ at m/z 228 and [2CHCA+H]$^+$ at m/z 379, dominated the spectrum. By contrast, SALDI showed only a few peaks in the low-mass range, generated from ions of citric acid adducts (□) and impurity (●). The detection limit for the two peptides was in the sub-fmol level (100 fmol [Sar1, Thr8]-angiotensin II gave S/N~38), pointing to a highly sensitive detection of peptides with the chip.

It can be appreciated that the low background in the mass window below 500 Da suggests this calcinated surface can be useful for analysis of small molecules. FIGS. 2c and 2d show mass spectra for three amino acids of Lys, His and Arg on the calcinated surface and with CHCA matrix, respectively. In the presence of CHCA, matrix adducted ions dominated the spectrum while sample ions were swamped by CHCA fragment ions including [CHCA-H$_2$O+H]$^+$ at m/z 172 and [CHCA-CO$_2$+H]$^+$ at m/z 146, which are very close to ArgH (m/z 175) and LysH$^+$ (m/z 147). On the calcinated surface, sample ions were dominant in the spectrum with much improved noise level. The ion intensity was high and signals related to citric acid adducts and impurities appeared with low abundance. The results clearly demonstrate the effectiveness of the calcinated surface for MS analysis of small molecules. This feature would be particularly useful for metabonomics study and drug discovery where high throughput screening of small compounds is constantly required.

Figure 3:
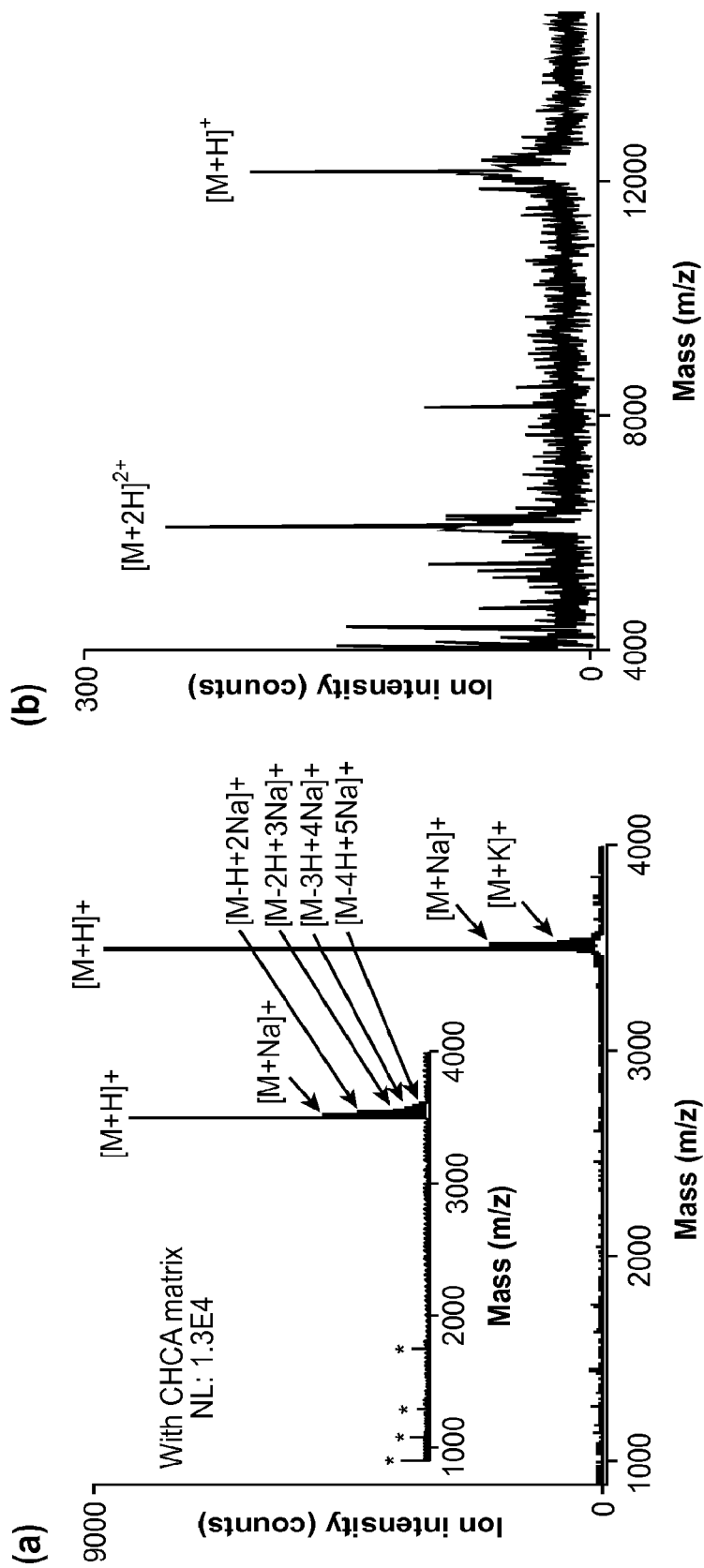
FIG. 3 shows a mass spectra for peptide and protein with SALDI on the calcinated glass surface as follows: (a) Insulin chain b, 20 pmol with 10 mM citric acid; the inset spectrum was obtained with CHCA matrix on steel MALDI plate under the same conditions; *: CHCA related ions; and (b) cytochrome c from bovine heart, 40 pmol in 10 mM citric acid.

The feasibility of using the calcinated surface for SALDI-MS analysis of large molecules was also explored. FIG. 3 shows the SALDI mass spectra of insulin b chain (oxidized, MW 3495.9) and cytochrome c (from bovine heart, MW 12,327). A very clean background was achieved for SALDI analysis of these large biomolecules, especially for insulin b chain. In comparison, matrix related ions were found in the mass region higher than 900 Da when CHCA was used (inset). In addition, several multi-sodium adducted ions for the peptide, including [M+Na]$^+$, [M−H+2Na]$^+$, [M−2H+3Na]$^+$, [M+−3H+4Na]+ and [M−4H++5Na]$^+$ were observed with CHCA matrix due to existence of two sulfonic groups in the peptide framework. SALDI with calcinated surface, on the other hand, produced only protonated sample ions and single alkali metal adducted ions, including [M+Na]$^+$ and [M+K]$^+$. The ion intensity ratio of protonated ions to single sodium adducted ions was about 4.7, which was much higher than 2.8 in the MALDI-MS with CHCA. This result suggests that SALDI on the calcinated silicate surface, with assistance of citric acid, tends to produce protonated sample ions and can effectively suppress the generation of alkali metal adducted ions, and therefore greatly simplify the mass spectrum for peptide identification. Cytochrome c can also be identified by using the calcinated surface with SALDI. In accordance with an exemplary embodiment, the protonated pseudomolecular ions ([M+H]$^+$) and the double charged ions ([M+2H]$^{2+}$) of the protein were found, showing that the dynamic range of the substrate spans a large mass window that includes both amino acids and small proteins.

In addition to large mass dynamic range, calcinated substrates are highly stable and have exhibited excellent long-term durability. There was no detectable loss of material in SPR spectroscopic study of incubation of the chips for hours with different buffers including Tris-HCl, NaCl and PBS. SALDI activity and performance of the substrates have no significant change after storage in air for months. Additionally, the surface can be repeatedly used as many as 10 cycles with minimal loss in ionization efficiency, and readily modified by silanes without deterioration on SALDI-performance (supplement). These attractive features provide variety of choices to further facilitate LDI activity, sample deposition, and selective capture of analyte by tailoring surface properties with chemical modification.

Understanding Performance-Determining Factors on Calcinated Surface

Figure 4:
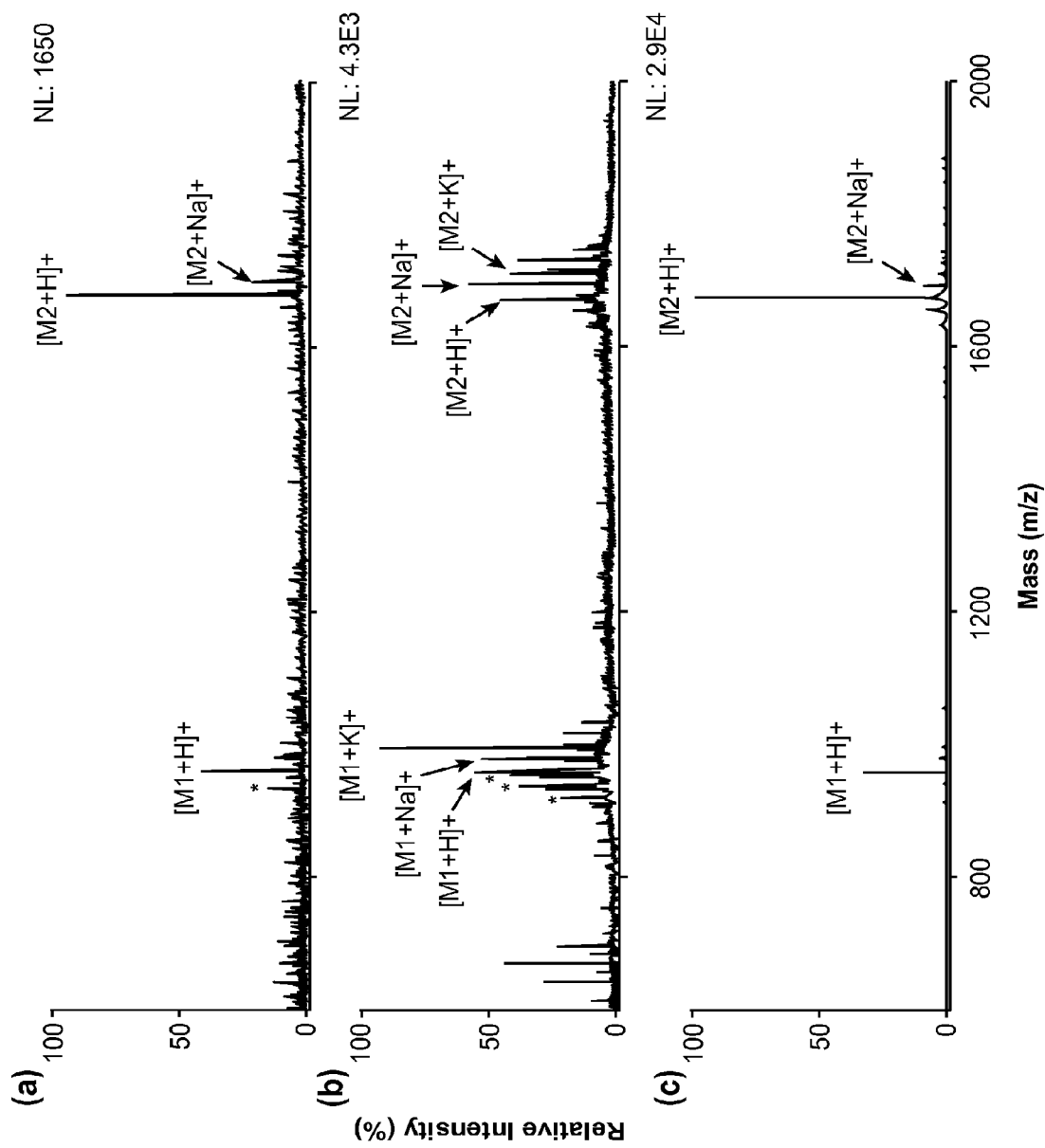
FIG. 4 shows a SALDI-MS analysis of two peptides on different substrates as follows: (a) Au-covered SST; (b) calcinated film on Au-covered SST; and (c) calcinated film on Au-covered SST with 10 mM citric acid. Conditions: samples: [Sar$^1$, Thr$^8$]-angiotensin II (MW=956.1) and neurotensin (MW=1672), 20 pmol each, and wherein Spectrum (c) contains 10 mM citric acid in the sample. (*) Fragment ions generated from analytes.

In accordance with an exemplary embodiment, experimental parameters that affect LDI on calcinated surface were investigated to understand the process and improve the performance. In the case of DIOS-MS, it has been proposed that properties of porous silicon such as UV absorption, surface morphology and thermoconductivity play important roles in the LDI process. However, silicate has no strong absorption at 337 nm of the N$_2$ laser and it is clear that LDI on this surface was not a direct result of UV-absorption of the glassy layer since silicate film fabricated on glass slides was SALDI inactive and yielded no signal in MS detection. In addition, neither bare glass cover slips nor HF-etched glass cover slips showed any activity for SALDI. Thus, in accordance with an exemplary embodiment, the Au layer is essential to the LDI process. In accordance with an exemplary embodiment, bare gold surface was not effective for inducing LDI. FIG. 4 shows mass spectra generated from SALDI on Au-covered SST and calcinated Au-covered SST chips. LDI efficiency remained very low for Au-covered SST. Ion intensities of protonated ions for [Sar$^1$, Thr$^8$]-angiotensin II (M1) was only about 563 counts (FIG. 4a). In comparison, the calcinated substrate showed a much enhanced LDI for [M1+H]$^+$ with ion intensity increasing to 2170, which is an almost 4-fold increase (FIG. 4b). SALDI-MS for neurotensin (M2) gave similar results. Furthermore, abundant alkali-adducted analyte ions, including [M+Na]$^+$ and [M+K]$^+$, were produced on the calcinated surface and showed higher ion intensities relative to the protonated ones. In accordance with an exemplary embodiment, the alkali metal ions are thought to originate from sodium silicate in the calcinated film, suggesting some degree of ion exchange and charge separation are involved in the LDI process.

In accordance with an exemplary embodiment, fragmentation of the sample ions on the calcinated chip appeared to be excessive. To suppress the fragmentation and increase production of protonated ions, an external proton donor was utilized. FIG. 4c shows the performance of SALDI on calcinated films with addition of 10 mM citric acid in the peptide solution. An extremely clean background in the mass spectrum was resulted, and production of alkali-adducted ions and fragment ions was highly suppressed. Protonated analyte ions dominated in the spectrum, and ion intensities for [M1+H] and [M2+H]$^+$ increased by 4.4 and 15.8 times with citric acid, corresponding to nearly 8 and 30 times increase of signal-to-noise ratio, respectively. No obvious improvement of LDI was observed though on the bare Au-SST surface with the external proton donor. The concentration of citric acid in sample solution was optimized for LDI and ion abundance of protonated analyte ions was found to increase with the increase of citric acid under 10 mM concentration (supplement). In accordance with an exemplary embodiment, it became difficult to obtain an MS signal from sample spots when the concentration of citric acid exceeded 20 mM. When 100 mM citric acid was used, the MS response completely disappeared. It can be appreciated that this may be attributed to co-crystallization of citric acid with analytes on the calcinated surface, which forms a thick layer on top of the substrate and thus results in reduction of the LDI efficiency. The increase of sample-spot thickness can also cause problem in thermal desorption of the deposited components due to limited depth of laser penetration through the film.

The effect of laser fluence on LDI on calcinated chips was investigated. The laser threshold on this surface was determined to be 1920, which was about 20% higher than that for MALDI with CHCA matrix. In comparison, more than 60% increase of laser fluence is required to achieve MS signals for peptide in DIOS and SALDI with porous alumina relative to CHCA matrix. The lower laser fluence as compared to other substrates demonstrates a higher LDI efficiency on the calcinated surface. In accordance with an exemplary embodiment, the ion signal increased with laser intensity, reaching the climax at the laser intensity of 2250. The signal then decreased rapidly with the application of higher laser fluence (supplement). The decline of ion signal may be attributed to the damage of nanoscale calcinated layer by rapid heating at high laser fluence. It can be appreciated that this phenomenon was also observed in DIOS and SALDI on metals.

Surface Characterization and Possible Mechanism

Figure 5:
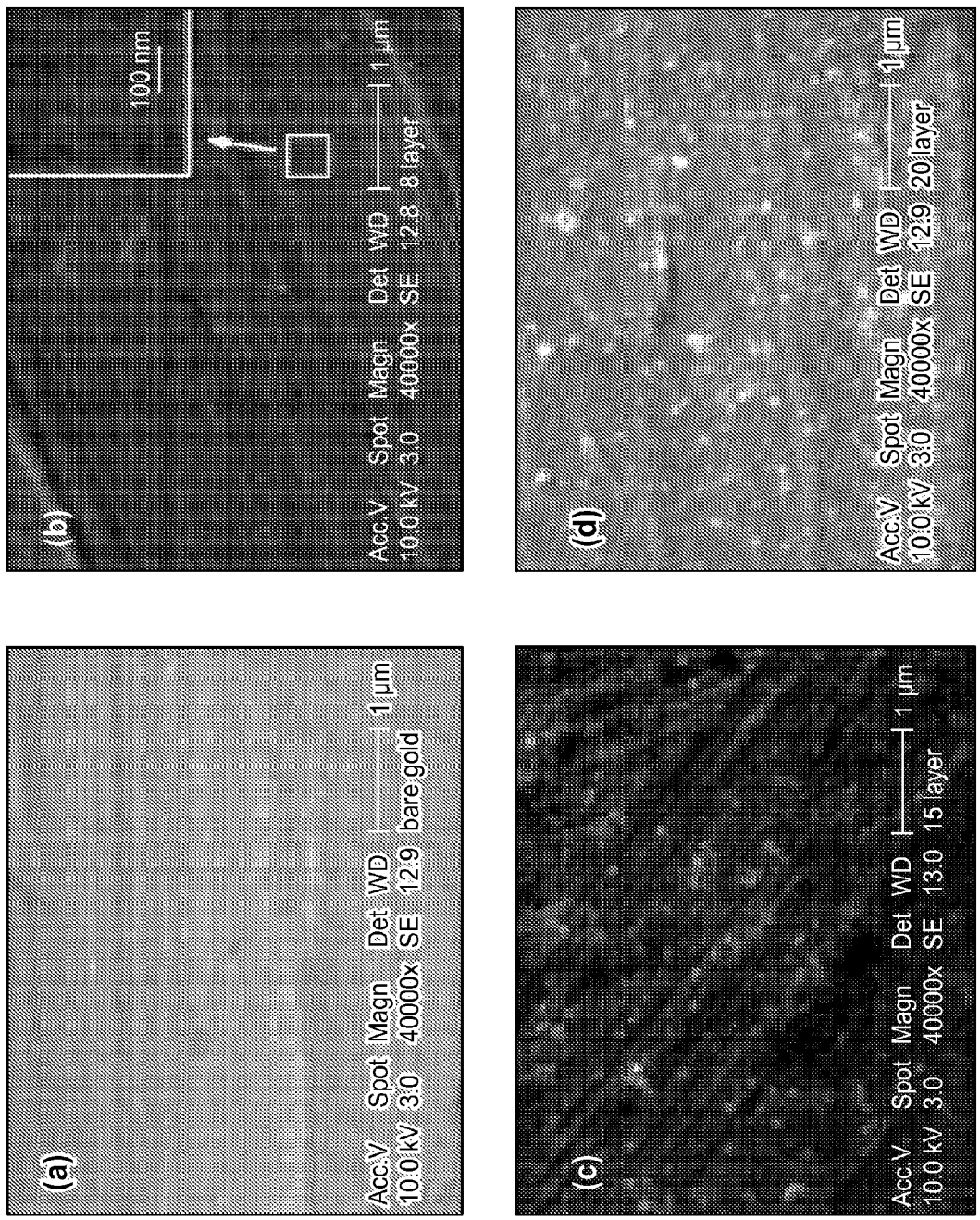
FIG. 5 shows SEM images of calcinated surface with different layers of silicate on gold surface deposited on a SST tape as follows: (a) bare Au surface, (b) 8 layers of silicate, (c) 15 layers of silicate, and (d) 20 layers of silicate, wherein the scale bar in the images is 1 μm, expect for image on the right top of (b), which is 100 nm.

Surface roughness has been suggested to affect LDI on solid surfaces. FIG. 5 shows the SEM images of the calcinated surface covered by 8, 15 and 20 layers of PAH/silicate. In accordance with an exemplary embodiment, a relative smooth surface was observed on the bare Au except repeated ridges and wrinkles arising from blunt irregularities of the SST. These irregular structures were also found on the calcinated film-covered SST substrates. For surfaces covered by the calcinated film, a relative rough superficial layer was obtained and no obvious fractures were found. Importantly, a porous structure in the nanometer scale (pore size less than 20 nm) was observed with high magnification (FIG. 5b inset). These pores may come from removal of organic components by calcination and localized shrinkage of the silicate layer after annealing. As more layers of silicate were deposited, the surface roughness increased and became dominating for 15 and 20 layers films with more nanometer-sized islands formed.

Figure 6:
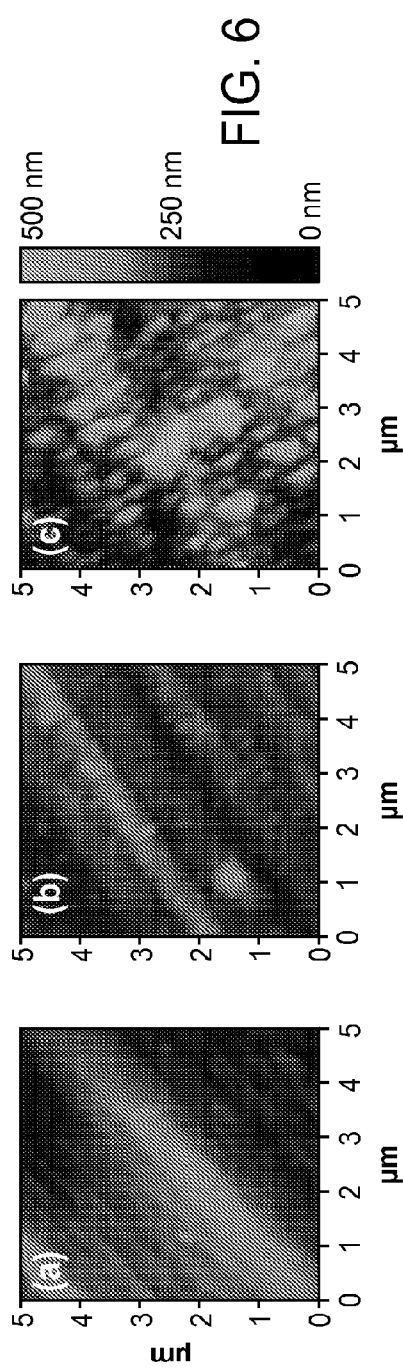
FIG. 6 shows AFM images of calcinated surface with different layers of silicate on gold substrate deposited on an SST tape as follows: (a) 5 layers of silicate, (b) 15 layers of silicate, and (c) 20 layers of silicate.

AFM was also used to examine the substrates (FIG. 6). The bright streaks, which appeared across the images, were the ridges and wrinkles observed in SEM images (FIG. 5). The surface roughness (RMS) for the calcinated film on an SST substrate was much higher than that for the same surface on glass slides. For instance, the RMS for surface with 5 layers of silicate on SST was 21.3±0.6 nm, while the RMS value for 6-layer silicate on glass slide was less than 4 nm. Additionally, increased RMS values were observed on substrates with more calcinated layers, where the RMS values for 15-layer and 20-layer silicate were 27.7±0.6 nm and 44.3±2.3 nm, respectively. The increased RMS would arise from the formation of nanostructured islands, which were also observed in SEM.

Figure 7:
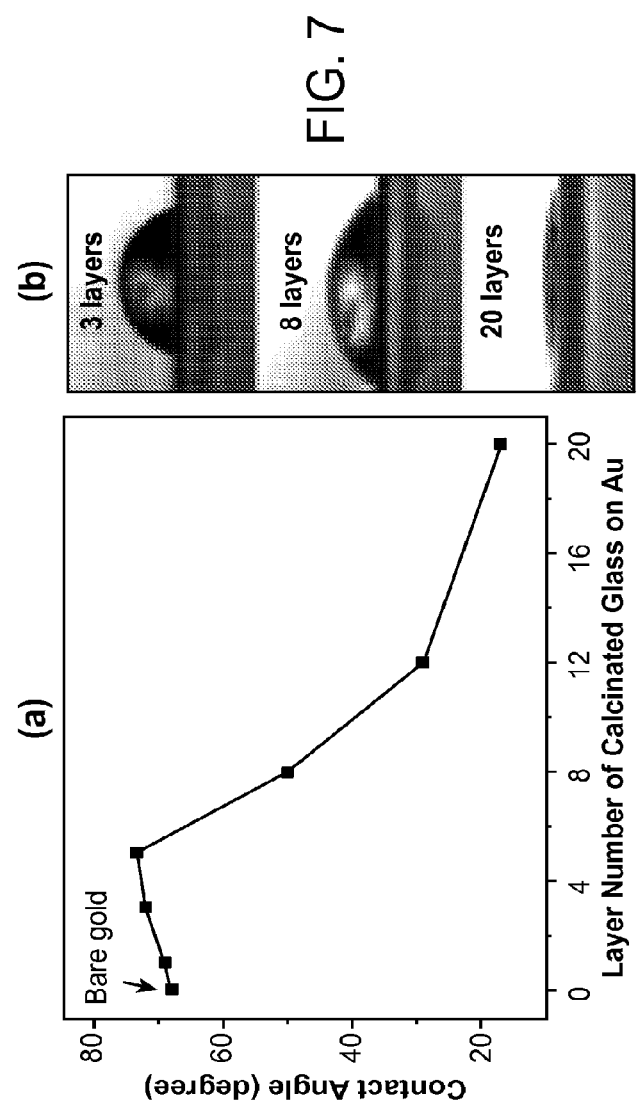
FIG. 7 shows contact angle measurements for calcinated silicate surfaces as follows: (a) contact angle of water on surfaces changes with layers of silicate; and (b) images of water droplets on surfaces with different layers of silicate.
Figure 12:
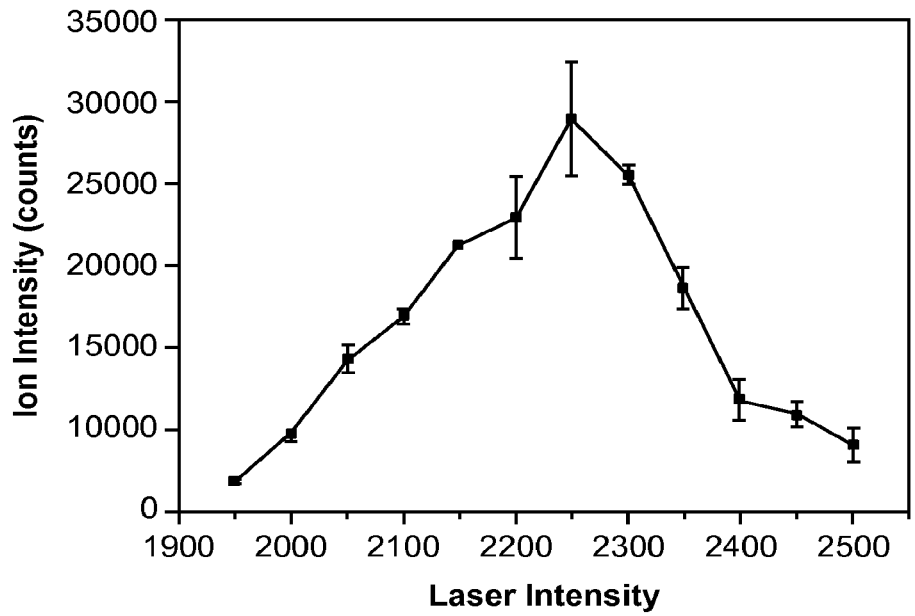
FIG. 12 is a chart showing the effect of laser fluence on ion intensity of protonated angiotensin. Mean and standard deviation from repeated measurements (n>3) are presented.
Figure 13:
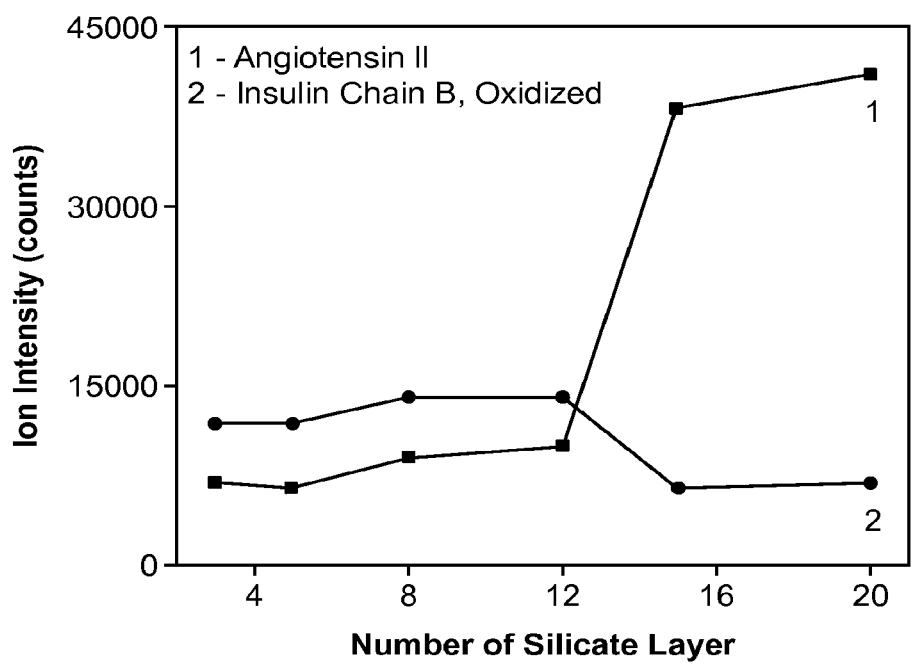
FIG. 13 are SALDI-MS analysis of peptides on substrates with different layers of silicate, wherein (1) angiotensin II; and (2) insulin chain b.

Surface hydrophobicity property of SALDI-substrates plays important role in desorption/ionization of analytes. Contact angle measurements were carried out to evaluate the surface hydrophilicity of the calcinated film with different numbers of deposited layers (FIG. 7). Bare Au-SST surface showed a contact angle of 68°. Sodium silicate glass is known for its high hydrophilicity and it can be appreciated that the surface becomes more hydrophilic with increasing number of silicate layers. However, it can be appreciated that the contact angle value increases slightly from 68° to 73° with the first 1-5 layers of (PAH/silicate) deposition. In accordance with an exemplary embodiment, an initial moderate increase of hydrophobicity can arise from introduction of free silanol groups at the surface. When the first several layers of silicate were coated, a single-layer structure film with random uncovered areas was formed due to uneven growth of polyelectrolytes. Silanol groups exposed at the surface exist as free hydroxyl groups, which lowers the affinity of water to the surface. As more layers of silicate were coated, the surface hydrophilicity increased remarkably. When 20 layers of silicate were fabricated, the contact angle was only 17° (FIG. 7). The silanol groups in multilayer structure are likely converted to hydrogen bonded hydroxyl groups, which promote water physisorption and therefore increase the hydrophilicity. In addition, the increase in surface roughness and sodium content for multilayer silicate can also contribute to the increase of hydrophilicity of the calcinated substrate.

In accordance with an exemplary embodiment, LDI on 15-layer and 20-layer silicate showed 5.8 and 6.3 times of enhancement in terms of ion abundance for [Sar1, Thr8]-angiotensin II relative to that on 5 layers of silicate (supplement Figure S6). It can be appreciated that the results verify that rough surfaces for the 15 and 20 layers enhance LDI. However, ion intensities for insulin b chain decreased by 47% and 44% on 15-layer and 20-layer surfaces as compared to that on the 5-layer substrate. Thus, this suggests a rather complex process for peptide ionization on the calcinated surface and other surface properties such as hydrophobicity may play an important role. Insulin b chain is known to be more hydrophobic than [Sar1, Thr8]-angiotensin II since insulin b chain shows a stronger retention in reversed-phase LC than [Sar1, Thr8]-angiotensin II (data not shown). The relative higher hydrophobicity of insulin b chain can cause poor dispersion of the molecules on a hydrophilic surface, especially a porous film. By contrast, [Sar1, Thr8]-angiotensin II, which is a hydrophilic peptide, tends to disperse well over the hydrophilic surface where higher abundant analyte ions were resulted. The "match of hydrophilicity" allows the molecules to penetrate effectively into pores on the surface, and therefore the efficiency of heat transfer from substrate to analytes is enhanced. It can be appreciated that the surface wetting property is important to manipulate LDI on a calcinated film, which favors samples with better dispersion on the surface.

The overall mechanism of LDI on a nanoscale calcinated film on Au could be complex and likely an electron-phonon collision/lattice heating phenomenon. The application of pulsed UV-laser onto the nanometer-scale Au layer leads to rapid thermalization of excited electrons, giving rise to a hot free electron gas that heats up the metal lattice through a collision mechanism or volume plasmon process. It can be appreciated that the calcinated film on Au plays a crucial role of confining the heat at local area due to its low heat conductivity. The localized heating promotes vaporization of the molecules and thus desorption of analytes. Porosity of the film and match of wetting property that leads to analyte penetration into the porous calcinated film are important. The LDI process can also be assisted by surface nanostructures of the calcinated layer including small islands and sharp tips, at which ion exchange and charge separation can be involved to produce analyte ions. It should be noted that thicker films (greater than 60 layers) attenuated the ion intensity, suggesting a delicately balanced role of the calcinated film between local confinement of heat and total insulation. The use of citric acid highly improves LDI performance for its role as an external proton donor and possibly as a "buffer" in heat transfer to enhance the "soft" desorption ionization for analyte ions.

In accordance with an exemplary embodiment, nanoscale calcinated films on Au are a highly attractive and promising substrate for SALDI-MS analysis of biomolecules including amino acids, peptides and small proteins. Low background noise and high LDI efficiency offers a new platform for mass spectrometric analysis with a large mass range. The calcinated silicate substrate has several advantages over other existing SALDI-substrates, including ease of fabrication and modification, high reusability, good reproducibility, long-term air stability, and low cost. The LDI on calcinated substrates appears to depend on laser induced thermal desorption, in which the thin Au layer plays a crucial role for energy absorption and heating whereas nanoscale silicate film is important for heat confinement to generate hot spots. It can be appreciated that surface hydrophilicity and roughness of the calcinated film are important factors that manipulate the performance. Existence of low concentration of citric acid in sample highly promotes protonation of analytes and suppresses ion fragmentation. As surface properties of glass can be easily manipulated by silane-based chemistry and the thin gold film is optically active, the LDI-MS with the calcinated substrates are amenable for integration with existing technologies such as microfluidics, microarray chips and many optical methods.

Figure 14:
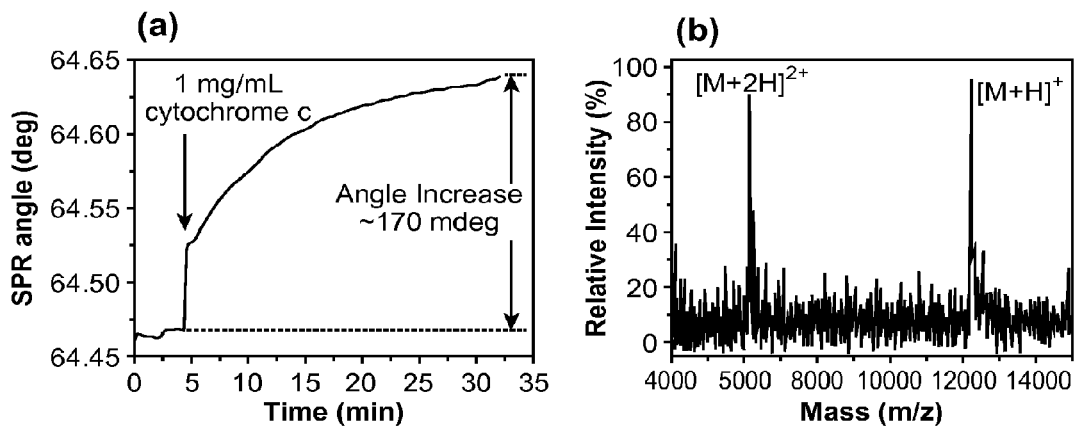
FIG. 14 shows a combination of SPR and SALDI-MS for the analysis of protein with calcinated substrate, wherein (a) SPR sensorgram of protein binding on calcinated substrate; (b) Direct SALDI-MS analysis of protein on calcinated substrate. Sample: 1 mg/mL cytochrome c; buffer: 0.1% TFA water solution containing 10 mM citric acid; substrate: 8-layer substrate.

In accordance with another exemplary embodiment, calcinated substrate on gold is also an excellent surface for SALDI-MS analysis of a broad range of biomolecules. It is also an ideal interface to integrate SALDI-MS with existing microscale separation and detection technologies such as microfluidics and microarrays. It can be appreciated that one of the most exciting feature of the calcinated substrate is its intrinsic property to couple with surface plasmon resonance (SPR) biosensors, which can offer highly sensitive, quantitative measurement of biomolecules in a real-time, label-free fashion. Therefore, calcinated film on gold-covered glass substrate can be used to investigate the binding of proteins by SPR monitoring, followed by direct SALDI-MS detection of absorbed proteins. In accordance with an exemplary embodiment, this function has been demonstrated with both SPR spectroscopy and SPR imaging technique as set forth below. The latter is significant to high throughput analysis in the proteomics studies. The SPR sensorgram in FIG. 14a shows the interaction between cytochrome c and the calcinated silicate film by SPR spectroscopy. SPR resonance angle increased about 170 mdeg after incubation of 1 mg/mL cytochrome c on the calcinated substrate, indicating adsorption of the protein on the chip. After the chip was removed from the flowcell, SALDI-MS was used to detect the presence of protein on the calcinated surface. FIG. 14b shows the SALDI-MS detection with the calcinated surface. Two peaks appeared at m/z 6120 and m/z 12225, which were assigned as $[M+2H]^{2+}$ and $[M+H]^+$ for cytochrome c (M), respectively. This result clearly confirms the binding of the protein on the surface and its identification, offering both quantitative and structural information for the target molecules.

Figure 15:
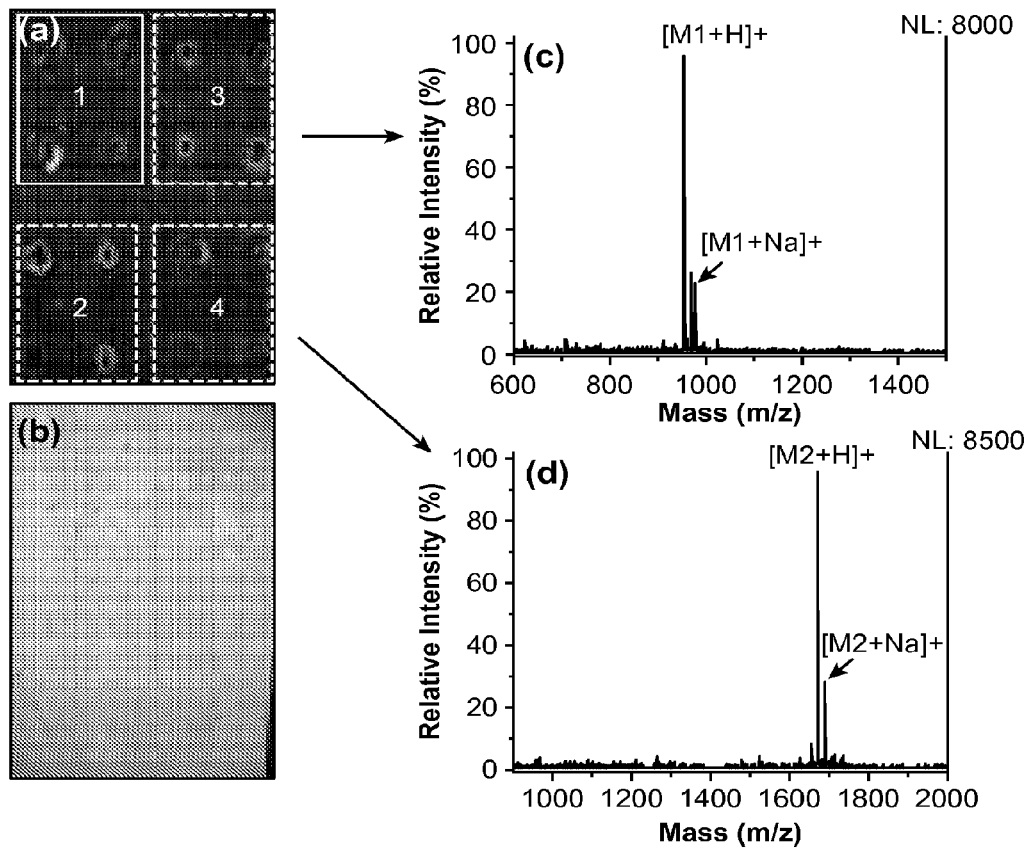
FIG. 15 shows a combination of SPR imaging and SALDI-MS for the analysis of peptide and protein, wherein (a) SPR imaging of protein and peptide spots on calcinated substrate, p-polarized. Spots: 1: Control; 2: cytochrome c; 3: [Sar$^1$, Thr$^8$]-angiotensin II; 4: neurotensin (MW=1672); (b) imaging of protein and peptide spots on calcinated substrate with s-polarization; (c) SALDI-MS detection on spot 3 ([Sar$^1$, Thr$^8$]-angiotensin II, MW=956.1); and (d) SALDI-MS detection on spot 4 (neurotensin, MW=1672).

Calcinated substrate is also a highly desirable platform for microarray analysis, in which combination of SPR imaging analysis and SALDI-MS detection can be performed for high throughput analysis. FIG. 15a shows p-polarized SPR imaging of 4×4 spot array with the calcinated substrate in air. Four samples including control, cytochrome c, [Sar$^1$, Thr$^8$]-angiotensin II and neurotensin are nano-deposited in Zone 1, 2, 3 and 4, respectively, generating 4 individual 2×2 spot arrays with 50 nL sample used for each spot. The diameter of each spot was about 1 mm. That sample spots can't be observed with s-polarization (FIG. 15b) clearly demonstrates the images in FIG. 15a are true SPR images. SALDI-MS detection was directly performed for the sample spot on the calcinated chip. FIGS. 15c and 15d show the SALDI-MS spectra for [Sar$^1$, Thr$^8$]-angiotensin II and neurotensin, respectively. Two peptides were identified according to their mass-to-charge value in the spectrum. Additionally, with SALDI-MS detection, a very clean background can be achieved. This is very significant as the current method of choice, MALDI-MS, gives high background signal due to use of organic matrix.

Figure 16:
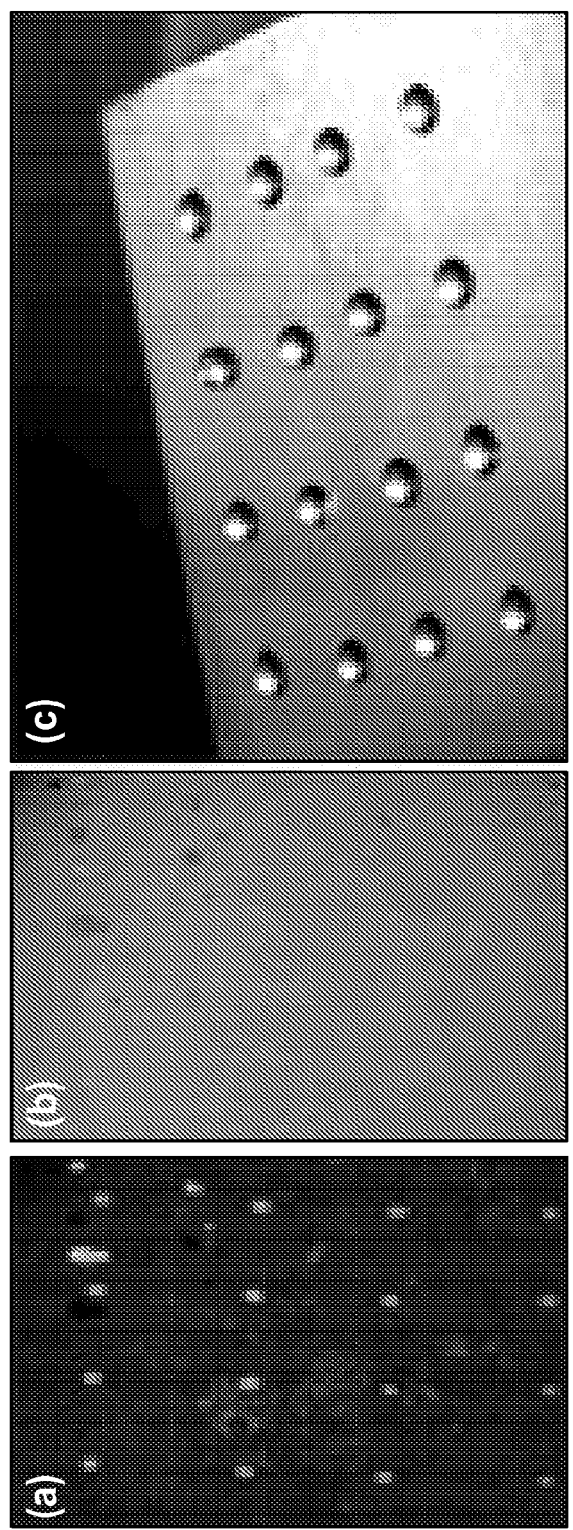
FIG. 16 shows a SDS array on calcinated substrate, wherein (a) SPR imaging of SDS array on calcinated substrate, p-polarity; (b) SPR imaging of SDS array on calcinated substrate, s-polarity; and (c) microscopy picture of SDS array with sample.

Calcinated substrate can also serve as a versatile platform for analysis of biomolecules after surface tailoring by chemical modification. Hydrophobic substrate can be obtained by modification of calcinated surface with octadecyltrichlorosilane. This surface can facilitate sample preparation prior to SALDI-MS by desalting and reduction of spot-size. FIG. 16 showed different images of a protein array on the hydrophobic calcinated substrate. FIG. 16a is the SPR image of the array (4×4 spot array) on calcinated substrate while FIG. 16b is an image with s-polarization for comparison. The SPR image shows the array with high contrast, indicative of great feasibility of SPR imaging analysis using this chip. The diameter of each spot is about 500 μm. FIG. 16c shows the microscopic image of the array after sample deposition. This method can promote sample deposition on hydrophobic surface, allowing direct sample analysis with SALDI-MS detection.

It can be appreciated that our results clearly show that calcinated substrate is an excellent interface for integrating SPR techniques (including SPR spectroscopy and SPR imaging) with mass spectrometry (including MALDI or SALDI-MS). SPR and MS operate on an orthogonal detection principle, and can be performed for different analytical purpose. Combination of SPR sensor with SALDI-MS can facilitate the analysis of biomolecular recognition and interaction on the SPR sensor chips. SALDI-MS can used for direct identification of retained biomolecules on the calcinated chip and simplify the sample preparation. Combination of microarray technique with SPR imaging and SALDI-MS can promote high throughput analysis, providing not only quantitative but also identification information for the target molecules.

It will be understood that the foregoing description is of the preferred embodiments, and is, therefore, merely representative of the article and methods of manufacturing the same. It can be appreciated that many variations and modifications of the different embodiments in light of the above teachings will be readily apparent to those skilled in the art. Accordingly, the exemplary embodiments, as well as alternative embodiments, may be made without departing from the spirit and scope of the articles and methods as set forth in the attached claims.

What is claimed is:

1. A method of forming a calcinated silicate film for laser desorption ionization mass spectrometry, the method comprising:
    fabricating a layer of gold onto a substrate;
    alternately depositing layers of poly(allylamine hydrochloride) (PAH) and a sodium silicate solution onto a surface of the layer of gold;
    calcinating the alternately deposited layers of PAH and sodium silicate solution to form a calcinated nanofilm, the calcinated nanofilm having a thickness of 2 to 50 nanometers with a porosity of at least one nanometer;
    introducing a tailoring surface property to the calcinated nanofilm; and
    performing matrix-free laser desorption ionization mass spectrometry (LDI-MS) and/or surface-assisted laser desorption ionization (SALDI-MS) analysis of biomolecules on the calcinated nanofilm.

2. The method of claim 1, wherein the PAH has a concentration of 1 mg/mL with a pH of 8.0, and the sodium silicate solution has a concentration of 22 mg/mL, with a pH of 9.5.

3. The method of claim 1, comprising:
    immersing the gold layer in an ethanol solution followed by rinsing with ethanol and DI water.

4. The method of claim 1, comprising:
    alternately depositing 15 to 20 layers of PAH and sodium silicate solution onto the gold layer.

5. The method of claim 1, wherein the step of calcinating the alternately deposited layers of PAH and sodium silicate solution is performed at a temperature of 450° C.

6. The method of claim 1, comprising:
controlling a thickness of a layer of the calcinated nanofilm at 1 nm resolution.

7. The method of claim 1, wherein a 15-layer calcinated nanofilm after calcination has a thickness of 20 nm.

8. The method of claim 1, comprising:
introducing the tailoring surface property to the calcinated nanofilm by silylation chemistry, desalting, sample preconcentration and/or selective capture of analytes.

9. The method of claim 1, comprising:
integrating the calcinated silicate film with microfluidic, microarray chip, and/or optical methods.

10. The method of claim 1, comprising:
integrating surface plasmon resonance (SPR) spectroscopy and SPR imaging with the LDI-MS and/or the SALDI-MS on the calcinated silicate film.

11. The method of claim 10, comprising:
combining a SPR sensor with the SALDI-MS for facilitating analysis of biomolecular recognition and interaction on SPR sensor chips.

12. The method of claim 10, comprising:
using SALDI-MS for direct identification of retained biomolecules on the calcinated nanofilm.

13. The method of claim 12, comprising:
combining a microarray technique with the SPR imaging and the SALDI-MS to promote high throughput analysis, and
providing quantitative and identification information for target molecules.

14. The method of claim 1, comprising:
functionalizing the layer of gold with 3 MPA ethanol solution before alternately depositing the layers of poly(allylamine hydrochloride) (PAH) and sodium silicate solution onto the surface of the layer of gold.

* * * * *